United States Patent [19]

Jaeggi et al.

[11] B 4,014,920
[45] Mar. 29, 1977

[54] N-CINNAMYLCARBAMIC ACID ESTERS

[75] Inventors: Knut Alfred Jaeggi, Basel; Franz Ostermayer, Riehen; Herbert Schröter, Fullinsdorf, all of Switzerland

[73] Assignee: Ciba-Geigy Corporation, Ardsley, N.Y.

[22] Filed: June 4, 1973

[21] Appl. No.: 367,092

[44] Published under the second Trial Voluntary Protest Program on April 13, 1976 as document No. B 367,092.

[30] Foreign Application Priority Data

June 8, 1972   Switzerland ............... 8505/72
Apr. 18, 1973   Switzerland ............... 5634/73

[52] U.S. Cl. ................ 260/471 C; 260/240 R; 260/240 A; 260/243 B; 260/247.2 A; 260/268 C; 260/293.76; 260/307 A; 260/326.43; 260/348 R; 260/348 A; 260/349; 260/465 D; 260/465 E; 260/470; 260/471 R; 260/479 R; 260/553 R; 260/562 A; 260/570.7; 260/515 R; 260/600 R; 424/246; 424/248.54; 424/267; 424/272; 424/274; 424/309; 424/319; 424/322; 424/330

[51] Int. Cl.² .............................. C07C 125/06
[58] Field of Search ..................... 260/471 C

[56] References Cited

UNITED STATES PATENTS 3,712,927   1/1973   Howe et al. ................ 260/471 C
3,864,398   2/1975   Suzuki et al. ............... 260/471 C Primary Examiner—James A. Patten
Attorney, Agent, or Firm—Joseph G. Kolodny; John J. Maitner; Theodore O. Groeger

[57] ABSTRACT

Amines of the formula

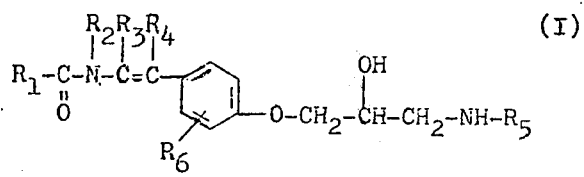

wherein $R_1$ is lower alkyl, lower alkoxy or amino, $R_2$ is hydrogen or lower alkyl, $R_3$ is hydrogen, lower alkyl, carboxyl or lower alkoxycarbonyl, $R_4$ is hydrogen or lower alkyl, $R_5$ is lower alkyl, aryl-lower alkyl or optionally functionally modified carboxy-lower alkyl and $R_6$ denotes halogen, trifluoromethyl, lower alkyl, lower alkenyl, lower alkoxy, lower alkenyloxy, nitro, lower alkoxymethyl, carbamoyl, N-lower alkylcarbamoyl, nitrile, lower alkinyloxy or hydrogen, and their salts block cardiac and vascular β-receptors the are useful in the treatment of arrhythenias and angina pectoris and as intermediates for, especially for pharmaceutically active substances.

13 Claims, No Drawings

N-CINNAMYLCARBAMIC ACID ESTERS

The invention relates to new amines of the formula

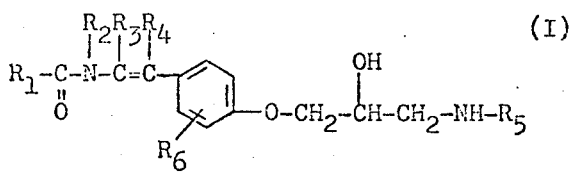

wherein $R_1$ is lower alkyl, lower alkoxy or amino, $R_2$ is hydrogen or lower alkyl, $R_3$ is hydrogen, lower alkyl, carboxyl or lower alkoxycarbonyl, $R_4$ is hydrogen or lower alkyl, $R_5$ is lower alkyl, aryl-lower alkyl or optionally functionally modified carboxy-lower alkyl and $R_6$ denotes halogen, trifluoromethyl, lower alkyl, lower alkenyl, lower alkoxy, lower alkenyloxy, nitro, lower alkoxymethyl, carbamoyl, N-lower alkylcarbamoyl, nitrile, lower alkinyloxy or hydrogen, and to processes for their manufacture.

In the preceding and following text, a lower radical is understood in particular as a radical with up to 7 C atoms, above all with up to 4 C atoms.

Lower alkyl $R_1$, $R_2$, $R_3$ and $R_4$ preferably has up to 7 C atoms, above all up to 4 C atoms, such as straight or branched butyl, pentyl, hexyl or heptyl bonded in any desired position, but especially iso- or n-propyl, ethyl and above all methyl.

Lower alkoxy $R_1$ and lower alkoxy in lower alkoxycarbonyl $R_3$ preferably has up to 7 C atoms, above all up to 4 C atoms, and is thus preferably straight or branched butoxy, pentyloxy, hexyloxy or heptyloxy bonded in any desired position, or above all iso- or n-propoxy, ethoxy or especially methoxy.

By amino $R_1$ there is to be understood primary, secondary and tertiary amino. Secondary and tertiary amino $R_1$ is preferably lower alkylamino or di-lower alkyl-amino, possible lower alkyl radicals being especially those mentioned for $R_1$–$R_4$, and the two lower alkyl radicals in di-lower alkylamino being identical or different. As secondary and tertiary amino $R_1$ there should be especially be mentioned: straight or branched monobutylamino and dibutylamino, butyl-propylamino, butyl-ethylamino, butyl-methylamino, propyl-ethylamino and propyl-methylamino, the butyl being bonded in any desired position, and above all monoisopropylamino and diisopropylamino, monopropylamino and dipropylamino, ethyl-methylamino, ethylamino and especially diethylamino, methyl-amino and dimethylamino. Alkyleneamino groups should furthermore be mentioned as tertiary amino $R_1$, and in these the alkylene radical can also be interrupted by hetero-atoms and/or be substituted. Such alkyleneamino radicals $R_1$ are especially optionally C-methylated pyrrolidino, piperidino, morpholino, thiomorpholino, piperazino, N'-methylpiperazino or N'-β-(hydroxyethyl)-piperazino radicals.

Lower alkoxycarbonyl $R_3$ is preferably lower alkoxycarbonyl which contains, as the lower alkoxy radical, one of the lower alkoxy radicals mentioned and singled out as $R_1$, such as, especially, ethoxycarbonyl and methoxycarbonyl.

Lower alkyl $R_5$ preferably has up to 7 C atoms, above all up to 4 C atoms, and is unbranched or preferably branched, especially branched at the α-C atom, and is, for example, sec.-butyl or especially tert.-butyl or above all isopropyl.

Aryl-lower alkyl $R_5$ preferably has up to 12 C atoms, above all up to 10 C atoms, and is unbranched or preferably branched in lower alkyl part, especially branched at the α-C atom of the lower alkyl part. The aryl part is, in particular, a phenyl radical which is optionally substituted several-fold or especially once by lower alkyl, such as the lower alkyl indicated for $R_1$–$R_4$, lower alkoxy, such as the lower alkoxy indicated for $R_6$, halogen, such as the halogen indicated for $R_6$, or trifluoromethyl, but is preferably unsubstituted. Examples of aryl-lower alkyl $R_3$ are 1-methyl-3-phenyl-propyl and especially 1-methyl-2-phenylethyl.

Optionally functionally modified carboxy-lower alkyl preferably has up to 7 C atoms, above all up to 4 C atoms, in the lower alkyl part and is unbranched or preferably branched, especially branched at the α-C atom. Optionally functionally modified carboxy-lower alkyl is thus preferably carboxymethyl, 2-(2-carboxy)-propyl, 2-(4-carboxy)-butyl or especially 2-carboxyethyl or above all 2-(3-carboxy)propyl, which are preferably functionally modified at the carboxyl group. The optionally functionally modified carboxyl group is, for example, free, esterified or amidised carboxyl or nitrile.

Esterified carboxyl is, for example, carboxyl esterified with an aliphatic alcohol. Aliphatic alcohols are those in which the hydroxyl group is bonded to a C atom which is not a member of an aromatic system. Examples of suitable aliphatic alcohols are cycloalkanols, such as those with 3–7, especially 5–7, ring members, for example cyclo-propanol, cyclopentanol, cyclohexanol and cycloheptanol, cyclo-alkyl-lower alkanols which contain, for example, the above cycloalkyl parts, such as cyclopentyl-methanol, cyclohexyl-methanol, 2-cyclohexyl-ethanol and cycloheptyl-methanol, phenyl-lower alkanols, such as 2-phenylethanol and benzyl alcohol, wherein phenyl radicals can also be substituted by halogen, lower alkyl or lower alkoxy, such as those mentioned above, and especially lower alkanols, such as n-propanol, isopropanol, straight-chain or branched butanol, pentanol, hexanol or heptanol and especially methanol or ethanol. Thus, esterified carboxyl is above all methoxycarbonyl or ethoxycarbonyl.

Amidised carboxyl is substituted or unsubstituted carbamoyl. Substituted carbamoyl, for example, has the formula —CO—NR$_7$R$_8$, wherein $R_7$ is hydrogen or lower alkyl, and $R_8$ is lower alkyl, or $R_7$ and $R_8$ together are lower alkylene, oxa-lower alkylene, thia-lower alkylene or aza-lower alkylene. Lower alkyl is especially as mentioned above.

Lower alkylene is branched or, in particular, straight-chain lower alkyklene with, in particular, 2–7, above all 4–6, C atoms in the alkylene chain and, together with the N atom to which the lower alkylene is bonded, in particular represents pyrrolidino or piperidino.

Oxa-lower alkylene is branched or, in particular, straight-chain oxa-lower alkylene with, in particular, 4 or 5 C atoms in the oxaalkylene chain and, together with the N atom to which the oxa-lower alkylene is bonded, in particular represents morpholino.

Thia-lower alkylene is branched or, in particular, straight-chain thia-lower alkylene with, in particular, 4 or 5 C atoms in the thiaalkylene chain and, together with the N atom to which the thia-lower alkylene is bonded, in particular represents thiomorpholino or 2,6-dimethylthiomorpholino.

Aza-lower alkylene is branched or straight-chain aza-lower alkylene with, in particular, 2-6, above all 4-6, C atoms in the azaalkylene chain and, together with the N atom to which the aza-lower alkylene is bonded, in particular represents piperazino, N'-methyl-piperazino or N'-(β-hydroxy-ethyl)-piperazino.

Substituents $R_6$ which differs from hydrogen are preferably bonded in the 2-position to the propoxy radical. Further, the following apply: halogen is, for example, fluorine, bromine and especially chlorine. Lower alkyl in particular has the meaning indicated for $R_1$–$R_4$. Lower alkenyl has, for example, up to 7 C atoms, above all 2 to 4 C atoms, such as vinyl, methallyl and especially propenyl and allyl. Lower alkoxy is in particular lower alkoxy wherein the lower alkyl part has the remaining indicated for $R_1$–$R_4$, such as ethoxy, iso- or n-propoxy and especially methoxy. Lower alkenyloxy has, for example, up to 7 C atoms, especially 3 or 4 C atoms, in the lower alkenyl part, such as methallyloxy or above all allyloxy. Lower alkoxymethyl in particular contains, in the lower alkyl part, the radicals indicated and singled out for $R_1$–$R_4$. N-lower alkylcarbamoyl contains, as lower alkyl, in particular the radicals indicated and singled out for $R_1$–$R_4$. Lower alkinyloxy is, for example, propargyloxy.

The new compounds possess valuable pharmacological properties. Thus they block cardiac β-receptors, as can be shown in determining the antagonism of tachycardia after 0.5 μg/kg of d/l-isoproterenol sulphate administered intravenously to narcotised cats, on intravenously administering 0.1 to 2 mg of the new compounds/kg; they block vascular β-receptors, as can be shown in determining the antagonism of vasodilation after 0.5 82 g/kg of d/l-isoproterenol sulphate administered intravenously to narcotised cats, on intravenous administration of 3 or more mg of the new compounds/kg, and they block cardiac β-receptors, as can be shown in determining the tachycardia after 0.005 μg/ml of d/l-isoproterenol sulphate applied to isolated guinea pig hearts in vitro, at a concentration of 0.02 to 2 μg of the new compounds/ml.

The new compounds are therefore useful as cardioselective antagonists of adrenergic β-receptor stimulants, for example for the treatment of arrhythmias and angina pectoris. They are however also useful as valuable intermediate products for the manufacture of other useful substances, especially pharmaceutically active compounds.

The new amines are however also useful as starting substances for the manufacture of other useful substances, especially pharmacologically active substances. Thus, for example, the new amines of the formula I can be converted by hydrogenation of the double bond in the side chain in the usual manner, for example by catalytic hydrogenation, for example with hydrogen in the presence of a noble metal catalyst, such as platinum oxide or palladium on charcoal, if desired under elevated pressure and/or at elevated temperature, into amines of the formula

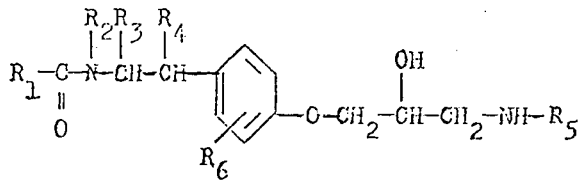

(I')

which show the same mode of action and similar strength of action as the amines of the formula I according to this application.

Compounds to be singled out are amines Ia of the formula I, wherein $R_1$ is lower alkyl or lower alkoxy, $R_2$ is hydrogen or lower alkyl, $R_3$ is hydrogen, lower alkoxycarbonyl or carboxyl, $R_4$ is hydrogen or lower alkyl with up to 4 C atoms, $R_5$ is a α-branched lower alkyl or a group of the formula

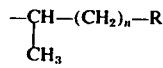

wherein n is 0, 1 or 2 and R is phenyl optionally substituted by $R_6$, carboxyl, esterified carboxyl, such as lower alkoxy-carbonyl, amidised carboxyl, such as free carbamoyl, N-lower alkylcarbamoyl, N,N-di-lower alkylcarbamoyl, N,N-lower alkylenecarbamoyl, N,N-oxalower alkylenecarbamoyl, N,N-thia-lower alkylene-carbamoyl, N,N-azo-lower alkylenecarbamoyl or nitrile and $R_6$ is hydrogen, halogen, lower alkoxy, lower alkenyl or lower alkenyloxy.

Compounds to be very particularly singled out are amines Ib of the formula I, wherein $R_1$ is lower alkyl with up to 4 C atoms or lower alkoxy with up to 4 C atoms, $R_2$ is hydrogen, methyl or ethyl, $R_3$ is hydrogen, carbomethoxy, carboethoxy or carboxyl, $R_4$ is hydrogen or lower alkyl with up to 3 C atoms, $R_5$ is α-branched lower alkyl with 3 to 6 C atoms or a group of the formula

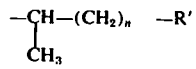

wherein n' is 0 or 1 and R' is benzyl optionally substituted by $R_6$, or is carboxyl, methoxycarbonyl, ethoxycarbonyl, carbamoyl, N-methylcarbamoyl, N,N-dimethylcarbamoyl, pyrrolidino-carbonyl, piperidinocarbonyl, morpholinocarbonyl, thio-morpholinocarbonyl, piperazinocarbonyl, N'-methylpiperazino-carbonyl or nitrile, and $R_6$ is hydrogen, chlorine, bromine, lower alkoxy with up to 4 C atoms, lower alkenyl with 2 to 5 C atoms or lower alkenyloxy with 3 to 5 C atoms.

Amongst the amines Ib of the formula I, amines Ic of the formula I should be singled out, wherein $R_1$ is ethyl or methyl or lower alkoxy with up to 4 C atoms, such as n-butoxy, n-propoxy, ethoxy or methoxy, $R_2$ is hydrogen or methyl, $R_3$ is hydrogen, carboxyl, carbomethoxy or carboethoxy, $R_4$ is hydrogen, methyl or ethyl, $R_5$ is α-branched lower alkyl with 3 or 4 C atoms or a group of the formula

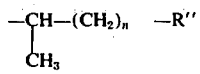

wherein $n'$ is 0 or 1 and $R''$ is benzyl which is optionally substituted by $R_6$, or is methoxycarbonyl, carbamoyl or nitrile, and $R_6$ denotes hydrogen, methoxy or ethoxy, chlorine, allyl, methallyl or propenyl-1, allyloxy or methallyloxy.

Amongst the amines Ic of the formula I, amines Id of the formula I should be singled out very particularly, wherein $R_1$ is methyl, methoxy, ethoxy or n-butoxy, $R_2$ is hydrogen, $R_3$ is hydrogen or carbomethoxy, $R_4$ is hydrogen or methyl, $R_5$ is isopropyl, tert.-butyl, 2(3-phenyl)butyl, 2-(1-carbamoyl)-propyl or 2-(1-cyano)-propyl and $R_6$ is hydrogen, methoxy, chlorine, allyloxy or allyl, especially 1-[p-(2-methoxycarbonyl-aminovinyl)-phenoxy]-2-hydroxy-3-(2-ethoxycarbonyl-1-methyl-ethylamine)-propane, 1-[4-(2-acetylaminovinyl)-2-allyloxy-phenoxy]-2-hydroxy-3-isopropylamino-propane, 1-[p-(2-ethoxy-carbonylaminovinyl)-phenyl]-2-hydroxy-3-tert.-butylamino-propane, 1-[p-(2-methoxycarbonylaminovinyl)-phenoxy]-2-hydroxy-3-(2-cyano-1-methyl-ethylamino)-propane, 1-[p-(2-methoxy-carbonylaminovinyl)-phenoxy]-2-hydroxy-3-(2-carbamoyl-1-methyl-ethylamino)-propane, 1-[p-(2-n-butoxycarbonylamino-vinyl)-phenoxy]-2-hydroxy-3-isopropylamino-propane, 1-[p-(2-methoxycarbonylaminovinyl)-phenoxy]-2-hydroxy-3-(1-methyl-3-phenyl-propylamino)-propane, 1-[p-(2-acetylaminovinyl)-phenoxy]-2-hydroxy-3-(2-carbamoyl-1-methyl-ethylamino)-propane, 1-[p-(2-acetylaminovinyl)-phenoxy]-2-hydroxy-3-(2-cyano-1-methyl-ethylamino)-propane, 1-[2-methoxy-4-(2-methoxycarbonyl-aminovinyl)-phenoxy]-2-hydroxy-3-isopropylaminopropane, 1-[4-(2-acetylaminovinyl)-2-methoxy-phenoxy]-2-3-isopropyl-aminopropane, 1-[2-allyl-4-(2-acetylaminovinyl)-phenoxy]-2-hydroxy-3-isopropylamino-propane, 1-[2-allyl-4-(2-methoxy-carbonylaminovinyl)-phenoxy]-2-hydroxy-3-isopropylamino-propane, 1-[p-(2-acetylamino-propen-1-yl)-phenoxy]-2-hydroxy-3-isopropylamino-propane, 1-[p-(2-methoxycarbonylamino-propen-1-yl)-phenoxy]-2-hydroxy-3-isopropylamino-propane, 1-[p-(2-propionylaminovinyl)-phenoxy]-2-hydroxy-3-isopropylamino-propane, 1-[4-(2-methoxycarbonylaminovinyl)-2-chlorophenoxy]-2-hydroxy-3-isopropylamino-propane, 1-[4-(2-propionylamino-vinyl)-2-methoxy-phenoxy]-2-hydroxy-3-isopropylamino-propane, 1-[p-(2-acetylaminovinyl)-phenoxy]-2-hydroxy-3-tert.-butyl-amino-propane, 1-[p-(2-acetylaminovinyl)-phenoxy]-2-hydroxy-3-isopropylamino-propane, 1-[p-(2-acetylamino-2-carbomethoxy-vinyl)-phenoxy]-2-hydroxy-3-isopropylamino-propane and very particularly 1-[p-(2-methoxycarbonylaminovinyl)-phenoxy]-2-hydroxy-3-isopropylamino-propane, which blocks the cardiac β-receptors, as can be shown on determining and antagonism of tachycardia afer 0.5 μg/kg of d/l-isoproterenol sulphate administered intravenously to narcotised cats, on intravenous administration of 0.03 to 1 mg of the compound/kg, blocks the vascular β-receptors, as can be shown on determining the antagonism of vasodilation after 0.5 μg/kg of d/l-isoproterenol sulphate administered intravenously to narcotised cats, on intravenous administration of 3 or more mg of the compound/kg, and blocks the cardiac β-receptors, as can be shown on determining the tachycardia after 0.005 μg/ml of d/l-isoproterenol sulphate applied to isolated guinea pig hearts in vitro, at a concentration of 0.03 to 1 μg of the compound/ml.

The new compounds are obtained according to methods which are in themselves known-reacting a compound of the formula II

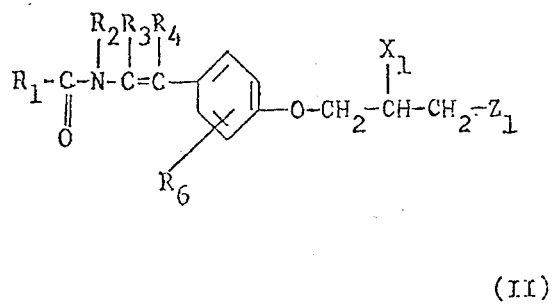

(II)

with a compound of the formula III

(III)

wherein $R_1$ to $R_6$ have the above meanings and one of the radicals $Z_1$ and $Z_2$ is amino and the other is a reactive esterified hydroxyl group Z and $X_1$ is hydroxyl, or $Z_1$ together with $X_1$ forms an epoxy group.

A reactive esterified hydroxyl group is especially a hydroxyl group esterified with a strong inorganic or organic acid, above all a hydrogen halide acid, such as hydrochloric acid, hydrobromic acid or hydriodic acid, or sulphuric acid, or by a strong organic sulphonic acid, such as a strong aromatic sulphonic acid, for example benzenesulphonic acid, p-bromobenzenesulphonic acid or p-toluenesulphonic acid. Thus, $Z_1$ in particular represents chlorine, bromine or iodine.

This reaction is carried out in the usual manner. When using a reactive ester as the starting material, the reaction is preferably carried out in the presence of a basic condensation agent and/or with an excess of amine. Suitable basic condensation agents are, for example, alkali metal hydroxides, such as sodium hydroxide or potassium hydroxide, alkali metal carbonates, such as potassium carbonate, and alkali metal alcoholates, such as sodium methylate, potassium ethylate and potassium tertiary-butylate.

In resulting compounds it is possible, within the scope of the definition of the final substances, to modify, introduce or split off substituents in the usual manner; alternatively, compounds obtained can be converted into other final substances in the usual manner.

Thus it is possible, in resulting compounds, to hydrolyze esterified carboxyl groups $R_3$ and functionally modified carboxyl groups forming a constituent of $R_5$ in the usual manner to give free carboxyl groups, preferably in the presence of a strong base, such as of a strong organic or above all inorganic base, preferably a metal base, for example an alkaline earth metal carbonate or alkali metal carbonate or above all an alkaline earth metal hydroxide or alkali metal hydroxide, for example in the presence of calcium hydroxide, sodium hydroxide or potassium hydroxide, or in the presence of a strong acid, for example of a strong mineral acid, especially of a hydrogen halide acid, for example hydrochloric acid or hydrobromic acid, or of sulphuric acid. If desired, oxidising agents, such as nitrous acid, can be added during the hydrolysis of the carbamoyl group.

The nitrile group, as a constituent of $R_5$, can also be hydrolysed to the carbamoyl group in the usual manner, for example as described above for the hydrolysis to the free carboxyl group. Equally it is also possible to convert the carbamoyl group into the nitrile group by dehydration in the usual manner, for example by heating and/or by the action of dehydrating agents.

Free carboxyl groups $R_3$ and those which form a constituent of $R_5$ can be esterified in the usual manner, for example by reaction with an appropriate alcohol, advantageously in the presence of an acid, such as of a mineral acid, for example sulphuric acid or hydrochloric acid, or in the presence of a water-binding agent, such as dicyclohexylcarbo-diimide, or by reaction with an appropriate diazo compound, for example a diazoalkane. The esterification can also be carried out by reaction of a salt, for example of an alkali metal salt, of the acid with a reactively esterified alcohol, for example a halide, such as the chloride, of the alcohol in question.

Functionally modified carboxyl groups as a constituent of $R_5$ can furthermore be converted into esterified or amidised carboxyl groups according to customary methods. Thus, resulting acid anhydrides, such as acid halides, for example acid chlorides, or ketenes, can be converted into esters or amides by reaction with an alcohol or with ammonia or a primary or secondary amine, if desired in the presence of acid-binding agents, such as organic or inorganic bases. By analogous reaction with an alcohol it is also possible to convert resulting nitriles into the corresponding imino-ethers, which can be hydrolysed in the usual manner to give the corresponding esters.

Furthermore, carbon dioxide can be removed from compounds obtained in which $R_3$ is carboxyl. The removal of carbon dioxide (decarboxylation) can be carried out in the usual manner, for example by heating, if appropriate in the presence of an inert solvent, for example of diphenyl ether or quinoline. It is however also possible to start from resulting compounds in which $R_3$ is an esterified carboxyl group, and to heat these in the presence of a hydrolysis catalyst, such as of an acid or basic agent, whereupon the corresponding free acid or a salt thereof is transiently obtained and then undergoes decarboxylation.

The reactions mentioned can, if appropriate, be carried out simultaneously or successively and in optional sequence.

The reactions mentioned are carried out in the usual manner in the presence or absence of diluents, condensation agents and/or catalytic agents, at lowered, ordinary or elevated temperature and optionally in a closed vessel.

Depending on the process conditions and on the starting substances, the final substances are obtained in the free form or in the form of their acid addition salts, which is also included in the invention. Thus, for example, basic, neutral or mixed salts and where appropriate also hemihydrates, monohydrates, sesquihydrates or polyhydrates thereof, can be obtained. The acid addition salts of the new compounds can be converted into the free compound in a manner which is in itself known, for example with basic agents, such as alkalis or ion exchangers. On the other hand, the resulting free bases can form salts with organic or inorganic acids. To maufacture acid addition salts, those acids which are suitable for forming therapeutically usable salts are used in particular. As examples of such acids there may be mentioned: hydrogen halide acids, sulphuric acids, phosphoric acids, nitric acid, fumaric acid and aliphatic, alicyclic, aromatic or heterocyclic carboxylic or sulphonic acids, such as formic acid, acetic acid, propionic acid, succinic acid, glycolic acid, lactic acid, malic acid, tartaric acid, citric acid, ascorbic acid, maleic acid or pyruvic acid, benzoic acid, anthranilic acid, p-hydroxybenzoic acid, salicylic acid or embonic acid, methanesulphonic acid, ethanesulphonic acid, hydroxyethanesulphonic acid, ethylenesulphonic acid, halogenobenzensulphonic acid, toluenesulphonic acid, cyclohexylaminesulphonic acid or sulphanilic acid.

These or other salts of the new compounds, such as picrates or perchlorates, can also be used for purifying the resulting free bases, by converting the free bases into salts, isolating these and again liberating the bases from the salts. Because of the close relationships between the new compounds in the free form and in the form of their salts, the free compounds are also to be understood, in the preceding and following text, where appropriate, to include the corresponding salts, as regards general sense and intended use.

The invention also relates to those embodiments of the process according to which a compound obtainable as an intermediate product at any stage of the process is used as the starting product and the missing process steps are carried out, or the process is stopped at any stage, or in which a starting substance is formed under the reaction conditions or in which a reactant is present in the form of its salts, if appropriate.

Depending on the choice of the starting substances and procedures, the new compounds can be in the form of optical antipodes or racemates or, if they contain at least two asymmetrical carbon atoms, also as racemate mixtures and/or as pure geometrical isomers or as mixtures thereof (isomer mixtures).

Resulting isomer mixtures can be separated into the two pure geometrical isomers in a known manner on the basis of the physico-chemical differences of the constituents, for example by chromatography on a suitable stationary phase, such as with a complex-forming heavy metal compound, for example with a silver compound, pre-treated silica gel or aluminum oxide, or by formation of a heavy metal addition compound, for example the silver nitrate complex, separation thereof into the addition compounds of the pure isomers, for example by fractional crystallisation, and subsequent liberation of the pure isomers.

Resulting pure isomers, for example trans-isomers, can be converted into the isomers of the opposite configuration, for example into the cis-isomers, in the usual manner, for example photochemically, for example by irradiation with light of suitable wavelengths, advantageously in a suitable solvent, such as an aliphatic hydrocarbon, or in the presence of a suitable catalyst.

Racemate mixtures can be separated into the two stereoisomeric (diastereomeric) pure racemates on the basis of the physico-chemical differences of the constituents, in a known manner, for example by chromatography and/or fractional crystallisation.

Resulting racemates can be separated according to known methods, for example by recrystallisation from an optically active solvent, by means of micro-organisms or by reaction with an optically active acid which forms salts with the racemic compound and separation of the salts obtained in this manner, for example on the basis of their differing solubilities into the diastereomers, from which the antipodes can be liberated by the action of suitable agents. Particularly customary optically active acids are, for example the D- and L-forms of tartaric acid, di-o-toluyltartaric acid, malic acid, mandelic acid, camphorsulphonic acid or quinic acid. Advantageously, the more active L-antipode is isolated.

Approximately, those starting substances are used for carrying out the reaction according to the invention which lead to the groups of final substances which have been particularly mentioned initially, and especially to the final substances which have been especially described or singled out.

The starting substances are known or can, if they are new, be obtained according to methods which are in themselves known.

Thus, the compounds of the formula II mentioned as starting substances are obtained, for example, by hydrolysing a compound of the formula

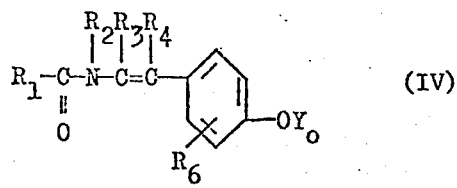

(IV)

wherein $R_1$, $R_2$, $R_3$, $R_4$ and $R_6$ have the indicated meanings, and $Y_o$ is a radical which can be split off by hydrolysis, for example one of those mentioned above, and reacting the compound of the formula V

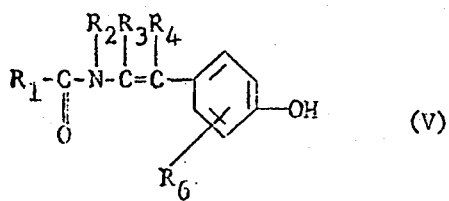

(V)

obtained in the usual manner with the compounds of the formula

(VI)

wherein $X_1$, $Z_1$ and Z have the indicated meanings.

The compounds of the formula XII, wherein $R_1$ denotes lower alkyl and $R_2$ and $R_3$ denote hydrogen, are obtained, in turn, by splitting hydrolytically an appropriate 2-$R_1$-4-(p-$OY_o$-benzylidene)-5(4H)-oxazolone of the formula

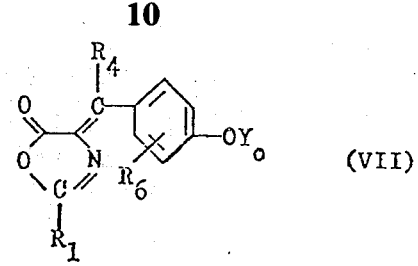

(VII)

wherein $R_1$, $R_4$, $R_6$ and $Y_o$ have the indicated meanings, and decarboxylating the resulting α-lower alkanoylaminocinnamic acid of the formula

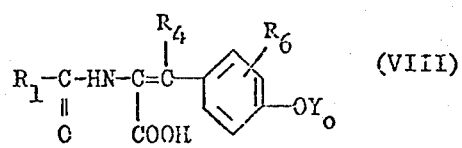

(VIII)

in the usual manner.

On the other hand, the compounds of the formula XII wherein $R_1$ is lower alkoxy or amino can be manufactured by rearranging, in the presence of an alcohol or amine of the formula $R_1H$, a p-$OY_o$-cinnamic acid azide of the formula

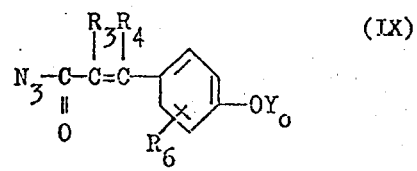

(IX)

wherein $R_3$, $R_4$, $R_6$ and $Y_o$ have the indicated meanings, which is obtainable from the corresponding p-$OY_o$-cinnamic acid by conversion into a halide thereof and subsequent reaction with a metal azide, for example with sodium azide, obtained in the usual manner with compounds of the formula

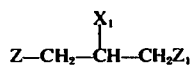

wherein $X_1$, $Z_1$ and Z have the indicated meanings.

The new compounds can be used as medicaments, for example in the form of pharmaceutical preparations, in which the compounds or their salts are present mixed with a pharmaceutical, organic or inorganic, solid or liquid excipient suitable, for example, for enteral or parenteral administration. Suitable substances for forming the excipient are those which do not react with the new compounds such as, for example, water, gelatine, lactose, starch, magnesium stearate, talc, vegetable oils, benzyl alcohols, gum, polyalkylene glycols, white petroleum jelly, cholesterol or other known medicinal excipients. The pharmaceutical preparations can, for example, be in the form of tablets, dragees, capsules, suppositories, ointments or creams or in a liquid form, as solutions, (for example as an elixir or syrup), suspensions or emulsions. They are optionally sterilised and/or contain auxiliaries, such as preservatives, stabilisers, wetting agents or emulsifiers, salts for regulating the osmotic pressure or buffers. They can also contain yet other therapeutically valuable substances. The preparations, which can also be used in veterinary medicine, are formulated according to customary methods.

The examples which follow explain the invention without, however, limiting it.

EXAMPLE 1

11.6 g (0.05 mol) of 1-[p-(2-acetylaminovinyl)-phenoxy]-2,3-epoxy-propane are dissolved in 100 ml of isopropanol, 4.25 ml (0.05 mol) of isopropylamine are added and thereafter the mixture is heated to the boil for 3 hours under reflux. It is then evaporated in vacuo and the resulting crude base is crystallised from ethyl acetate. 1-[p-(2-Acetylaminovinyl)-phenoxy]-2-hydroxy-3-isopropylaminopropane of melting point 144°–146°C is obtained.

On dissolving this in acetone and adding the calculated amount of anhydrous oxalic acid, the crystalline hydrogen oxalate, melting point 178°–179°C (after recrystallisation from methanol-ether), is obtained.

The N-cyclohexylsulphamate, melting point 129°–131°C (after recrystallisation from acetone), is obtained analogously.

The 1-[p-(2-acetylaminovinyl)-phenoxy]-2,3-epoxy-propane used as the starting material can be manufactured as follows.

75.8 g (0.3 mol) of 2-methyl-4-(p-acetoxy-benzylidene)-5(4H)-oxazolone are dissolved in a mixture of 725 ml of acetone and 281 ml of water and thereafter the solution is heated to the boil, under a reflux condenser, for 15 hours. Hereupon, a yellowish precipitate separates out. The reaction mixture is cooled and then filtered. The resulting crystals are recrystallised from acetone-water. p-Acetoxy-α-acetylaminocinnamic acid of melting point 236°–237°C is obtained.

26.3 g (0.1 mol) of p-acetoxy-α-acetylaminocinnamic acid, 50 ml of quinoline and 2 g of copper powder are heated to 160°–170°C for 3 hours, in the course of which carbon dioxide is evolved. Thereafter, the quinoline is distilled off in vacuo and the residual mass is taken up in ethyl acetate. After filtering off the copper powder, the ethyl acetate solution is extracted with 25 ml of 1 N hydrochloric acid and is then washed with water and sodium bicarbonate solution. The organic phase is dried over sodium sulphate and thereafter the solvent is removed by distillation in vacuo. The resulting oil, on crystallisation from ethyl acetate, yields p-(2-acetylaminovinyl)-acetoxybenzene of melting point 165°–166°C.

13.0 g (0.05 mol) of p-(2-acetylaminovinyl)-acetoxybenzene are suspended in 100 ml of absolute methanol, a solution of 2.8 g (0.05 mol) of sodium methoxide in 20 ml of absolute methanol is added and thereafter the mixture is warmed to 50°C for 15 minutes. It is then evaporated to dryness in vacuo. The resulting crude phenolate of p-(2-acetylaminovinyl)-phenol is heated with 65 ml of epichlorohydrin to the boil for 18 hours, under a reflux condenser and whilst stirring. Thereafter, the excess epichlorohydrin is removed by vacuum distillation. The residue is partitioned between water and ethyl acetate and the organic phase is siphoned off, dried over sodium sulphate and evaporated. After crystallisation of the crude product, thus obtained, from acetone-ether, 1-[p-(2-acetylaminovinyl)-phenoxy]-2,3-epoxy-propane of melting point 135°–137°C is obtained.

EXAMPLE 2

9.4 g (0.038 mol) of 1-[p-(2-methoxycarbonylaminovinyl)-phenoxy]-2,3-epoxy-propane are dissolved in 200 ml of isopropanol, 3.25 ml (0.038 mol) of isopropylamine are added and thereafter the mixture is heated to the boil for 3 hours, under a reflux condenser. It is then evaporated in vacuo and the resulting crude base is crystallised from acetoneether. 1-[p-(2-Methoxycarbonylaminovinyl)-phenoxy]-2-hydroxy-3-isopropylamino-propane of melting point 128°–129°C is obtained.

From this, after dissolving in acetone and adding the calculated amount of oxalic acid, the hydrogen oxalate, melting point 162°–164°C (after recrystallisation from acetone), is obtained.

The N-cyclohexylsulphamate, melting point 115°–116°C (after recrystallisation from acetone) and, using isopropanol as the solvent, the fumarate, melting point 163°–164°C (from methanol-isopropanol), are obtained analogously.

1-[p-(2-Methoxycarbonylaminovinyl)-phenoxy]-2,3-epoxy-propane, used as the starting material, can be obtained as follows:

41.2 g (0.02 mol) of p-acetoxy-cinnamic acid are suspended in 100 ml of benzene and 29 ml (0.4 mol) of thionyl chloride are added. The reaction mixture is heated to the boil under a reflux condenser for half an hour and thereafter the solvent and excess thionyl chloride are removed by distillation in vacuo. The crude p-acetoxy-cinnamic acid chloride which remains is dissolved in 200 ml of absolute dimethoxyethane, 39 g (0.6 mol) of sodium azide are added and thereafter the mixture is stirred for 48 hours at room temperature. The inorganic salts are then filtered off and the filtrate is concentrated in vacuo at 30°C. Hereupon, colourless crystals separate out. The crystallisation is completed by adding ether. p-Acetoxy-cinnamic acid azide of melting point 114°C (decomposition) is obtained.

23.1 g (0.1 mol) of p-acetoxy-cinnamic acid azide are suspended in 220 ml of absolute toluene and the suspension is slowly brought to the boil, whilst stirring. The evolution of nitrogen starts at approx. 80°C and is complete after boiling for half an hour. After cooling to room temperature, 8 ml (0.2 mol) of absolute methanol and a few drops of triethylamine are added. Thereafter, the mixture is heated under reflux for 18 hours, the solvent is distilled off in vacuo and the crystalline residue is dissolved in acetone. On addition of ether, p-(2-methoxycarbonylaminovinyl)-acetoxybenzene of melting point 133°–134°C is obtained.

6.8 g (0.035 mol) of p-(2-methoxycarbonylaminovinyl)-acetoxybenzene are suspended in 100 ml of absolute methanol, a solution of 1.9 g (0.035 mol) of sodium methoxide in 15 ml of absolute methanol is added and thereafter the mixture is warmed to 50°C for 15 minutes. It is then evaporated to dryness in vacuo. The resulting, crude phenolate of p-(2-methoxycarbonylaminovinyl)-phenol is heated with 35 ml of epichlorohydrin to the boil for 24 hours under a reflux condenser, whilst stirring. Thereafter, the excess epichlorohydrin is removed by vacuum distillation. The residue is partitioned between water and methylene chloride and the organic phase is separated off, dried over sodium sulphate and evaporated. After crystallisation of the crude product thus obtained, from acetoneether, 1-[p-(2-methoxycarbonylaminovinyl)-phenoxy]-2,3-epoxy-propane of melting point 125°–126°C is obtained.

EXAMPLE 3

Analogously to the description in Example 2, 3.93 g (0.0135 mol) of 1-[p-(2-n-butoxycarbonylaminovinyl)-phenoxy]-2,3-epoxy-propane, on reaction with 1.22 ml (0.0142 mol) of isopropylamine in 50 ml of isopropanol, yield 1-[p-(2-n-butoxy-carbonylaminovinyl)-phenoxy]-2-hydroxy-3-isopropylaminopropane of melting point 125°–126°C (from acetone-ether).

From this, its oxalate, melting point 155°–156°C (recrystallised from acetone) is obtained after dissolving in acetone and adding the calculated amount of oxalic acid.

The 1-[p-(2-n-butoxycarbonylaminovinyl)-phenoxy]-2,3-epoxy-propane used as the starting material can be manufactured as follows:

13.8 g (0.06 mol) of p-acetoxy-cinnamic acid azide are suspended in 100 ml of absolute toluene and the suspension is slowly brought to the boil whilst stirring. The evolution of nitrogen commences at approx. 80°C; it is complete after boiling for half an hour. After cooling to room temperature, 11.0 ml (0.12 mol) of absolute n-butanol and a few drops of triethylamine are added. Thereafter the mixture is heated under reflux for 18 hours, the solvent is distilled off in vacuo and the crystalline residue is dissolved in acetone. On addition of ether, p-(2-n-butoxycarbonylaminovinyl)-acetoxybenzene of melting point 90°–91°C (from ether), is obtained.

12.5 g (0.045 mol) of p-(2-n-butoxycarbonylaminovinyl)-acetoxybenzene, after dissolving in 75 ml of absolute methanol, addition of a solution of 2.43 g (0.045 mol) of sodium methoxide in 50 ml of methanol, heating to 50°C for 15 minutes and subsequent evaporation to dryness in vacuo, yield the crude sodium salt of p-(2-n-butoxycarbonylaminovinyl)-phenol. This is heated to the boil with 45 ml of epichlorohydrin for 24 hours under a reflux condenser, whilst stirring. Thereafter, the excess epichlorohydrin is removed by vacuum distillation. The residue is partitioned between water and methylene chloride and the organic phase is separated off, dried over sodium sulphate and evaporated. 1-[p-(2-n-Butoxycarbonylaminovinyl)-phenoxy]-2,3-epoxy-propane of melting point 120°C (from ether) is obtained.

EXAMPLE 4

Analogously to the description in Example 2, 2.5 g (0.01 mol) of 1-[p-(2-ethoxycarbonylaminovinyl)-phenoxy]-2,3-epoxy-propane, on reaction with 1.0 ml (0.01 mol) of tert.-butylamine in 50 ml of isopropanol, yield 1-[p-(2-carbethoxy-aminovinyl)-phenoxy]-2-hydroxy-3-tertiary -butylaminopropane as an oil. Its N-cyclohexyl-sulphamate, prepared in acetone, shows a melting point of 99°–100°C (from ether).

1-[p-(2-Ethoxy-carbonylaminovinyl)-phenoxy]-2,3-epoxy-propane used as the starting material, can be manufactured as follows:

10.2 g (0.044 mol) of p-acetoxy-cinnamic acid azide are suspended in 100 ml of absolute toluene and the suspension is slowly brought to the boil, whilst stirring. The evolution of nitrogen commences at approx. 80°C and is complete after boiling for half an hour. After cooling to room temperature, 5.15 ml (0.088 mol) of absolute ethanol and a few drops of triethylamine are added. Thereafter the mixture is heated for 18 hours under reflux, the solvent is distilled off in vacuo and the crystalline residue is dissolved in acetone. On addition of ether, p-(2-ethoxycarbonylaminovinyl)-acetoxybenzene of melting point 102°–104°C (from acetone) is obtained.

5.0 g (0.02 mol) of p-(2-ethoxycarbonylaminovinyl)-acetoxybenzene, after dissolving in 75 ml of absolute ethanol, addition of a solution of 1.36 g (0.02 mol) of sodium ethoxide in 10 ml of absolute ethanol, 15 minutes' heating to 50°C and subsequent evaporation to dryness in vacuo, yield the crude sodium salt of p-(2-ethoxycarbonylaminovinyl)-phenol. This is heated with 20 ml of epichlorohydrin to the boil for 24 hours under a reflux condenser and whilst stirring. Thereafter, the excess epichlorohydrin is removed by vacuum distillation. The residue is partitioned between water and methylene chloride and the organic phase is separated off, dried over sodium sulphate and evaporated. 1-[p-(2-Ethoxycarbonylaminovinyl)-phenoxy]-2,3-epoxy-propane of melting point 112–113°C (from ether) is obtained.

EXAMPLE 5

7.5 g (0.03 mol) of 1-[p-(2-methoxycarbonylaminovinyl)-phenoxy]-2,3-epoxypropane are dissolved in 75 ml of acetonitrile and added dropwise to a boiling stirred solution of 3.34 g (0.029 mol) of β-aminobutyric acid amide in 75 ml of aceto-nitrile. The mixture is stirred for 20 hours under reflux, the solvent is removed by distillation under reduced pressure and the oil which remains is partitioned between 350 ml of 0.1 N hydrochloric acid and 300 ml of ethyl acetate. The hydrochloric acid extract is separated off, rendered alkaline with sodium carbonate and extracted four times with 100 ml of ethyl acetate at a time. The organic phases are dried over sodium sulphate and evaporated under reduced pressure. The resulting oil yields 1-[p-(2-methoxycarbonylaminovinyl)-phenoxy]-2-hydroxy-3-(2-carbamoyl-1-methyl-ethylamino)-propane, of melting point 109°–111°C, from acetone acetate.

This substance, after dissolving in acetone and mixing with the calculated amount of N-cyclohexylsulphamic acid, yields its N-cyclohexylsulphamate, of melting point 141°–143°C (from methanol-acetone).

EXAMPLE 6

3.0 g (0.012 mol) of 1-[p-(2-methoxycarbonylaminovinyl)-phenoxy]-2,3-epoxypropane are dissolved in 25 ml of acetonitrile and added dropwise to a boiling stirred solution of 0.96 g (0.011 mol) of β-aminobutyronitrile in 20 ml of acetonitrile. The mixture is stirred for 20 hours under reflux, the solvent is removed by distillation under reduced pressure and the oil which remains is partitioned between 150 ml of 0.1 N hydrochloric acid and 100 ml of ethyl acetate. The hydrochloric acid extract is separated off, rendered alkaline with sodium carbonate and extracted four times with 50 ml of ethyl acetate at a time. The organic phases are dried over sodium sulphate and evaporated under reduced pressure. The resulting oil solidifies on cooling to give crystals of 1-[p-(2-methoxy-carbonylaminovinyl)-phenoxy]-2-hydroxy-3-(2-cyano-1-methyl-ethyl-amino)-propane of melting point 122°–123°c.

This compound, after dissolving in acetone and mixing with the calculated amount of oxalic acid, yields the oxalate of melting point 139°–140°C (from methanol-acetone).

EXAMPLE 7

2.49 g (0.01 mol) of 1-[p-(2-methoxycarbonylaminovinyl)-phenoxy]-2,3-epoxy-propane are dissolved in 25 ml of acetonitrile and added dropwise to a boiling stirred solution of 1.42 g (0.0095 mol) of 3-amino-1-phenylbutane in 20 ml of acetonitrile. The mixture is stirred for 20 hours under reflux, the solvent is removed by distillation under reduced pressure and the oil which remains is partitioned between 120 ml of 0.1 N hydrochloric acid and 100 ml of ethyl acetate. The hydrochloric acid extract is separated off, rendered alkaline with sodium carbonate and extracted four times with 50 ml of ethyl acetate at a time. The organic phases are dried over sodium sulphate and evaporated in vacuo. The resulting oil yields 1-[p-(2-methoxycarbonyl-aminovinyl)-phenoxy]-2-hydroxy-3-(1-methyl-3-phenyl-propyl)-amino propane of melting point 126°–127°C, from ethyl acetate.

This product, after dissolving in acetone and mixing with the calculated amount of oxalic acid, yields the oxalate of melting point 185°    186°C (from methanol-acetone).

EXAMPLE 8

15.6 g (0.05 mol) of 1-[p-(2-acetylamino-2-carbomethoxyvinyl)-phenoxy]-2,3-epoxy-propane are dissolved in 50 ml of absolute tetrahydrofurane, 4.25 ml (0.05 mol) of isopropylamine are added and thereafter the mixture is heated for 18 hours to the boil under a reflux condenser. It is then evaporated in vacuo and the resulting crude base is dissolved in ethyl acetate. The solution is extracted three times with 20 ml of 1 N hydrochloric acid at a time. The hydrochloric acid extracts are brought to pH 8 with sodium carbonate solution and the crude base which hereupon has separated out is extracted with ethyl acetate. The extract is washed with water, dried over sodium sulphate and evaporated in vacuo. 17 g of crude base are obtained as a brownish oil. This is dissolved in 20 ml of acetone and mixed with a solution of 9 g of N-cyclo-hexylsulphamic acid in 70 ml of acetone. After addition of ether, the N-cyclohexylsulphamate of 1-[p-(2-acetylamino-2-carbomethoxy-vinyl)-phenoxy]-2-hydroxy-3-iso-proylamino-propane, melting point 121°–125°C, is obtained.

1-[p-(2-Acetyl-amino-2-carbomethoxy-vinyl)-phenoxy]-2,3-epoxy-propane, used as the starting material, can be manufactured as follows:

23.2 g (0.1 mol) of 2-methyl-4-(p-acetoxy-benzylidene)-5(4H)-oxazolone are introduced into a solution of 4.6 g (0.2 gram-atom) of sodium in 200 ml of absolute methanol, whereby a red solution is obtained. This is heated to the boil under reflux for 3 hours and is subsequently evaporated in vacuo. The residue is dissolved in 150 ml of water and the solution is saturated with carbon dioxide. Hereupon, a yellowish product precipitates. This is filtered off, washed with water and dried in vacuo. After recrystallisation from methanol-ether, α-acetylamino-p-hydroxy-cinnamic acid methyl ester of melting point 172-174°C is obtained.

11.8 g (0.05 mol) of α-acetylamino-p-hydroxy-cinnamic acid methyl ester are dissolved in a solution of 2.7 g of sodium methoxide in 40 ml of absolute methanol and immediately evaporated to dryness in vacuo. The resulting crude phenolate of α-acetylamino-p-hydroxy-cinnamic acid methyl ester is heated to the boil with 40 ml of epichlorohydrin for 4 hours, under a reflux condenser and whilst stirring. Thereafter, the excess epichlorohydrin is removed by vacuum distillation. The residue is partitioned between water and ethyl acetate and the organic phase is syphoned off, dried over sodium sulphate and evaporated. 1-[p-(2-Acetylamino-2-carbomethoxy-vinyl)-phenoxy]-2,3-epoxy-propane is obtained as a yellowish oil.

EXAMPLE 9

4.9 g (0.017 mol) of 1-[2-allyl-4-(2-methoxycarbonyl-aminovinyl)-phenoxy]-2,3-epoxy-propane are heated for 3 hours with a solution of 1.57 ml (0.018 mol) of isopropylamine in 100 ml of isopropanol to 80°C under reflux. The mixture is then evaporated under reduced pressure and the resulting crude base is crystallised from acetone-ether. 1-[2-Allyl -4-(2-methoxycarbonylaminovinyl)-phenoxy]-2-hydroxy-3-isopropyl-amino-propane, of melting point 128°–129°C is obtained.

From this, after dissolving in isopropanol and mixing with the calculated amount of fumaric acid, the fumarate, of melting point 187°–188°C (from methanol-isopropanol) is obtained.

1-[2-Allyl-4-(2-methoxycarbonylaminovinyl)-phenoxy]-2,3-epoxy-propane, used as the starting material, can be obtained as follows:

118 g (0.058 mol) of 3-allyl-4-hydroxy-cinnamic acid are dissolved in 580 ml of 2 N sodium hydroxide solution, 800 g of ice are added and 120 g (1.16 mols) of acetic anhydride are introduced dropwise over the course of 15 minutes at 0°–5°C, whilst stirring. The crystals which have precipitated are then separated off, suction-dried and recrystallised from ethyl acetate. 3-Allyl-4-acetoxy-cinnamic acid of melting point 143°–144°C is thus obtained.

22.2 g (0.09 mol) of 3-allyl-4-acetoxy-cinnamic acid are suspended in 100 ml of benzene and 13.2 ml (0.18 mol) of thionyl chloride are added. The reaction mixture is heated to the boil for half an hour under a reflux condenser and thereafter the solvent and excess thionyl chloride are removed by distillation under reduced pressure. The residual crude 3-allyl-4-acetoxy-cinnamic acid chloride is dissolved in 100 ml of absolute 1,2-dimethoxyethane, 17.5 g (0.27 mol) of sodium azide are added and the mixture is subsequently stirred for 48 hours at room temperature. The inorganic salts are then filtered off and the filtrate is concentrated under reduced pressure at 30°C. Hereupon, colourless crystals separate out. The crystallisation is completed by adding ether. 3-Allyl-4-acetoxy-cinnamic acid azide of melting point 87°–89°C (decomposition) is obtained.

19.4 g (0.07 mol) of 3-allyl-4-acetoxy-cinnamic acid azide are suspended in 200 ml of absolute toluene and brought to the boil whilst stirring slowly. The evolution of nitrogen starts at approx. 80°C and is complete after boiling for half an hour. After cooling to room temperature, 5.8 ml (0.14 mol) of absolute methanol and a few drops of triethylamine are added. Thereafter the mixture is heated to refluxing temperature for 18 hours, the solvent is distilled off under reduced pressure and the residue is crystallised from ether. 2-Allyl-4-(2-methoxycarbonylaminovinyl)-acetoxybenzene of melting point 143°–144°C is obtained.

7.8 g (0.028 mol) of 2-allyl-4-(2-methoxycarbonylamino-vinyl)-acetoxybenzene are suspended in 100 ml of absolute methanol, a solution of 1.54 g (0.028 mol) of sodium methoxide in 15 ml of absolute methanol is added and thereafter the mixture is warmed to 50°C for 15 minutes. It is then evaporated to dryness under reduced pressure. The resulting crude sodium salt of 2-allyl-4-(2-methoxycarbonylaminovinyl) phenol is heated to the boil with 30 ml of epichlorohydrin for 24 hours under a reflux condenser and whilst stirring. Thereafter, the excess epichlorohydrin is removed by distillation under reduced pressure. The residue is partitioned between water and methylene chloride and the organic phase is separated off, dried over sodium sulphate and evaporated. After crystallisation of the crude product, thus obtained, from ether, 1-[2-allyl-4-(2-methoxycarbonylaminovinyl)-phenoxy]-2,3-epoxypropane of melting point 92°–94°C is obtained.

EXAMPLE 10

Analogously to the description in Example 9, 3.9 g (0.014 mol) of 1-[4-(2-acetylaminovinyl)-2-allyl-phenoxy]-2,3-epoxy-propane are reacted with 1.35 ml (0.015 mol) of isopropyl-amine in 80 ml of isopropanol. After crystallisation from acetone-ether, 1-[4-(2-acetylaminovinyl)-2-allyl-phenoxy]-2-hydroxy-3-isopropylamino-propane of melting point 134°C is obtained and, from this, its N-cyclohexylsulphamate of melting point 147°–148°C (from acetone).

1-[4-(2-Acetyl-aminovinyl)-2-allyl-phenoxy]-2,3-epoxypropane, used as the starting material, can be obtained as follows:

40.5 g (0.25 mol) of 3-allyl-4-hydroxy-benzaldehyde, 10.3 g of sodium acetate, 19.9 g of N-acetylglycine and 63.5 g of acetic anhydride are together heated for 30 minutes to 100°C and then for 2½ hours to the reflux temperature. The resulting solution is cooled to 0°C and the crystals which have separated out are filtered off, washed with water, dried in a vacuum desiccator and finally recrystallised from carbon tetrachloride. 2-Methyl-4-(4-acetoxy-3-allyl-benzylidene)-5(4H)-oxazolone of melting point 108°–109°C is obtained.

22.3 g (0.078 mol) of 2-methyl-4-(4-acetoxy-3-allyl-benzylidene)-5(4H)-oxazolone are dissolved in a mixture of 184 ml of acetone and 72 ml of water and the solution is subsequently heated to the boil for 15 hours under a reflux condenser. The bulk of the acetone is then distilled off under reduced pressure, whereupon crystallisation occurs. The crystals are filtered off and subsequently recrystallised from acetone. 4-(2-Acetylamino-2-carboxy-vinyl)-2-allyl-acetoxybenzene of melting point 204°–205°C is obtained.

11.4 g (0.037 mol) of 4-(2-acetylamino-2-carboxyvinyl)-2-allyl-acetoxybenzene are heated with 20 ml of quinoline and 0.6 g of copper powder for 3 hours to 160°–170°C, in the course of which carbon dioxide is evolved. Thereafter the quinoline is distilled off under reduced pressure and the remaining mass is taken up in ethyl acetate, the copper powder is filtered off and the ethyl acetate solution is extracted with 10 ml of 1 N hydrochloric acid, and washed with water and subsequently with sodium bicarbonate solution. The organic phase is dried over sodium sulphate and thereafter the solvent is removed by distillation under reduced pressure. From ethyl acetate-petroleum ether, the oil obtained yields 4-(2-acetylaminovinyl)-2-allyl-acetoxybenzene of melting point 116°–117°C.

5.0 g (0.019 mol) of 4-(2-acetylaminovinyl)-2-allyl-acetoxybenzene are suspended in 50 ml of absolute methanol, a solution of 1.04 g (0.0185 mol) of sodium methoxide in 15 ml of absolute methanol is added and the mixture is subsequently warmed to 50°C for 15 minutes. It is then evaporated to dryness in vacuo. The resulting crude sodium salt of p-(2-acetylaminovinyl)-2-allyl-phenol is heated to the boil with 20 ml of epichlorohydrin under a reflux condenser and whilst stirring. Thereafter, the excess epichlorohydrin is removed by distillation under reduced pressure. The residue is partitioned between water and methylene chloride and the organic phase is separated off, dried over sodium sulphate and evaporated. After crystallisation, from ethyl acetate, of the crude product thus obtained, 1-[4-(2-acetylaminovinyl)-2-allyl-phenoxy]-2,3-epoxypropane of melting point 135°–136°C is obtained.

EXAMPLE 11

4.2 g (0.015 mol) of 1-[2-methoxy-4-(2-methoxycarbonyl-aminovinyl)-phenoxy]-2,3-epoxy-propane are heated with a solution of 1.3 ml (0.016 mol) of isopropylamine in 100 ml of isopropanol to 80°C under reflux for 3 hours. The mixture is then evaporated in vacuo and the resulting crude base is crystallised from acetone-ether. 1-[2-Methoxy-4-(2-methoxy-carbonylaminovinyl)-phenoxy]-2-hydroxy-3-isopropylaminopropane, of melting point 109°–111°C is obtained.

From this, after dissolving in isopropanol and mixing with the calculated amount of fumaric acid, the fumarate of melting point 170°–171°C (from methanol-isopropanol) is obtained.

1-[2-Methoxy-4-(methoxycarbonylaminovinyl)-phenoxy]-2,3-epoxypropane, used as the starting material, can be obtained as follows:

34.0 g (0.145 mol) of 4-acetoxy-3-methoxy-cinnamic acid are suspended in 150 ml of benzene and 21 ml (0.290 mol) of thionyl chloride are added. The mixture is then heated to the boil, under a reflux condenser, for 30 minutes; thereafter, the solvent and excess thionyl chloride are removed by distillation under reduced pressure. The crude 4-acetoxy-3-methoxy-cinnamic acid chloride which remains is dissolved in 150 ml of absolute 1,2-dimethoxyethane, 28.3 g (0.435 mol) of sodium azide are added and the mixture is subsequently stirred for 48 hours at room temperature. The inorganic salts are then filtered off and the filtrate is concentrated under reduced pressure at 30°C, in the course of which colourless crystals separate out. The crystallisation is completed by adding ether. 4-Acetoxy-3-methoxy-cinnamic acid azide of melting point 93°–95°C (decomposition) is obtained.

20.1 g (0.077 mol) of 4-acetoxy-3-methoxy-cinnamic acid azide are suspended in 200 ml of absolute toluene and slowly brought to the boil whilst stirring. The evolution of nitrogen starts at approx. 80°C and is complete after boiling for half an hour. After cooling to room temperature, 6.25 ml (0.154 mol) of absolute methanol and a few drops of triethylamine are added. Thereafter the mixture is heated to the refluxing temperature for 18 hours, the solvent is distilled off under reduced pressure and the residue is crystallised from ether. 2-Methoxy-4-(2-methoxycarbonyl-aminovinyl)-acetoxybenzene of melting point 128°–129°C is obtained.

5.1 g (0.019 mol) of 2-methoxy-4-(2-methoxycarbonyl-aminovinyl)-acetoxybenzene are suspended in 75 ml of absolute methanol, a solution of 1.04 g (0.019 mol) of sodium methoxide in 15 ml of absolute methanol is added and the mixture is subsequently warmed to 50°C for 15 minutes. It is then evaporated to dryness in vacuo. The resulting crude sodium salt of 2-methoxy-4-(2-methoxycarbonylaminovinyl)-phenol is heated to the boil, with 20 ml of epichlorohydrin, for 24 hours under a reflux condenser and whilst stirring. Thereafter, the excess epichlorohydrin is removed by distillation under reduced pressure. The residue is partitioned between water and methylene chloride and the organic phase is separated off, dried over sodium sulphate and evaporated. After crystallisation from ether of the crude product thus obtained, 1-[2-methoxy-4-(2-methoxycarbonylaminovinyl)-phenoxy]-2,3-epoxypropane of melting point 122°-123°C is obtained.

EXAMPLE 12

4.3 g (0.016 mol) of 1-[4-(2-acetylaminovinyl)-2-methoxy-phenoxy]-2,3-epoxy-propane are heated to 80°C with a solution of 1.4 ml (0.016 mol) of isopropylamine in 100 ml of isopropanol for 3 hours under reflux. The mixture is then evaporated in vacuo and the crude base obtained is crystallised from isopropanol-ethyl acetate. 1-[4-(2-Acetyl-aminovinyl)-2methoxy-phenoxy]-2-hydroxy-3-isopropylamino-propane of melting point 139°-140°C is obtained.

From this, the fumarate of melting point 192°-193°C (from methanol-isopropanol) is obtained after dissolving in isopropanol and mixing with the calculated amount of fumaric acid. 1-[4-(2-Acetyl-aminovinyl)-2-methoxy-phenoxy]-2,3-epoxypropane, used as the starting material, can be obtained as follows:

152 g (1 mol) of 4-hydroxy-3-methoxy-benzaldehyde, 41 g of sodium acetate, 80 g of N-acetylglycine and 242 g of acetic anhydride are heated together for 30 minutes to 100°C and then for 2½ hours to the refluxing temperature. The resulting solution is cooled to 0°C and the crystals which have separated out are filtered off and washed with water. The crude 2-methyl-4-(3-methoxy-4-acetoxy-benzylidene)-5(4H)-oxazolone thus obtained is heated to the boil with 1,400 ml of acetone and 545 ml of water for 15 hours under a reflux condenser. Thereafter, the acetone is largely distilled off, whereupon the product crystallises out. After filtration, and washing with acetone, 4-acetoxy-α-acetylamino-3-methoxy-cinnamic acid of melting point 205°-206°C is obtained.

18.0 g (0.06 mol) of 4-acetoxy-α-acetylamino-3-methoxy-cinnamic acid are heated with 30 ml of quinoline and 1.2 g of copper powder to 160°-170°C for 3 hours, in the course of which carbon dioxide is evolved. Thereafter, the quinoline is distilled off under reduced pressure and the residual mass is taken up in ethyl acetate. After filtering off the copper powder, the ethyl acetate solution is extracted with 25 ml of 1 N hydrochloric acid and is then washed with water and subsequently with sodium bicarbonate solution. The organic phase is dried over sodium sulphate and thereafter the solvent is removed by distillation under reduced pressure. The resulting oil yields 4-(2-acetylaminovinyl)-2-methoxy-acetoxy-benzene, of melting point 169°-170°C, from ethyl acetate.

7.5 g (0.03 mol) of 4-(2-acetylaminovinyl)-2-methoxy-acetoxybenzene are suspended in 60 ml of absolute methanol a solution of 1.65 g (0.03 mol) of sodium methoxide in 15 ml of absolute methanol is added and thereafter the mixture is warmed to 50°C for 15 minutes. It is then evaporated to dryness in vacuo. The resulting crude sodium salt of 4-(2-acetylaminovinyl)-2-methoxy-phenol is heated to the boil with 40 ml of epichlorohydrin for 18 hours whilst stirring and under a reflux condenser. Thereafter the excess epichlorohydrin is removed by distillation under reduced pressure. The residue is partitioned between water and methylene chloride and the organic phase is separated off, dried over sodium sulphate and evaporated. After crystallisation of the crude product, thus obtained, from ethyl acetate, 1-[4-(2-acetyl-aminovinyl)-2-methoxy-phenoxy]-2,3-epoxy-propane of melting point 173°-174°C is obtained.

EXAMPLE 13

4.0 g (0.0146 mol) of 1-[2-chloro-4-(2-methoxycarbonyl-phenoxyl]-2,3-epoxy-propane are heated with a solution of 1.26 g (0.0146 mol) of isopropylamine in 100 ml of isopropanol to 80°C for 3 hours under reflux. The mixture is then evaporated in vacuo and the resulting crude base is crystallised from acetone-ether. 1-[2-Chloro-4-(2-methoxycarbonyl-aminovinyl)-phenoxy]-2-hydroxy-3-isopropylaminopropane of melting point 122°-123°C is obtained.

From this, the fumarate of melting point 150°-151°C (from methanol-isopropanol) is obtained after dissolving in isopropanol and mixing with the calculated amount of fumaric acid.

1-[2-Chloro-4-(2-methoxycarbonylaminovinyl)-phenoxy]-2,3-epoxypropane, used as the starting material, can be obtained as follows:

46.2 g (0.273 mol) of 3-chloro-4-hydroxy-benzaldehyde, 104 g (1 mol) of malonic acid, 140 ml of pyridine and 4 ml of piperidine are heated to 100°C for 2 hours, whilst stirring. The volatile constituents are distilled off under reduced pressure at 80°C and the residue is stirred with 800 ml of water. The resulting crystals are filtered off and recrystallised from methanol-water. 3-Chloro-4-hydroxy-cinnamic acid of melting point 180°-182°C is obtained.

104 g (0.525 mol) of 3-chloro-4-hydroxy-cinnamic acid are dissolved in 530 ml of 2 N sodium hydroxide solution, 800 g of ice are added and 107 g (1.05 mols) of acetic anhydride are introduced dropwise over the course of 15 minutes at 0°-5°C, whilst stirring. The crystals which have precipitated are then filtered off, suction-dried and recrystallised from alcohol-water. 4-Acetoxy-3-chloro-cinnamic acid of melting point 210°-213°C is obtained.

24.0 g (0.1 mol) of 4-acetoxy-3-chloro-cinnamic acid are suspended in 90 ml of benzene and 14.6 ml (0.2 mol) of thionyl chloride are added. The reaction mixture is heated to the boil for half an hour under a reflux condenser and thereafter the solvent and excess thionyl chloride are removed by distillation under reduced pressure. The residual crude 4-acetoxy-3-chloro-cinnamic acid chloride is dissolved in 100 ml of absolute 1,2-dimethoxyethane, 19.5 g (0.3 mol) of sodium azide are added and thereafter the mixture is stirred for 48 hours at room temperature. The inorganic salts are then filtered off and the filtrate is concentrated under reduced pressure at 30°C. Hereupon, colourless crystals separate out. The crystallisation is completed by adding ether. 4-Acetoxy-3-chloro-cinnamic acid azide of melting point 102°-103°C (decomposition) is thus obtained.

7.95 g (0.03 mol) of 4-acetoxy-3-chloro-cinnamic acid azide are suspended in 100 ml of absolute toluene and the suspension is slowly heated to the boil whilst stirring. The evolution of nitrogen begins at about 80°C and is complete after boiling for half an hour. After cooling to room temperature, 2.4 ml (0.06 mol) of absolute methanol and a few drops of triethylamine are added. Thereafter the mixture is heated to the refluxing temperature for 18 hours, the solvent is distilled off under reduced pressure and the residue is crystallised from ether. 2-Chloro-4-(2-methoxy-carbonylaminovinyl)-acetoxybenzene of melting point 128°–131°C is obtained.

5.7 g (0.021 mol) of 2-chloro-4-(2-methoxycarbonylamino-vinyl)-acetoxybenzene are suspended in 75 ml of absolute methanol. A solution of 1.14 g (0.021 mol) of sodium methoxide in 15 ml of absolute methanol is added and the reaction mixture is subsequently heated for 15 minutes to 50°C and evaporated to dryness under reduced pressure. The resulting crude sodium salt of 2-chloro-4-(2-methoxycarbonylaminovinyl)-phenol is heated to the boil with 20 ml of epichlorohydrin for 24 hours under a reflux condenser and whilst stirring. Thereafter, the excess epichlorohydrin is removed by distillation under reduced pressure. The residue is partitioned between water and methylene chloride and the organic phase is separated off, dried over sodium sulphate and evaporated. After crystallisation of the crude product, thus obtained, from ether, 1-[2-chloro-4-(2-methoxycarbonyl-amino-vinyl)-phenoxy]-2,3-epoxypro-propane of melting point 109°–111°C is obtained.

EXAMPLE 14

2.86 g (0.01 mol) of 1-[p-(2-methoxycarbonylamino-vinyl)-phenoxy]-3-chloro-propanol-2 are heated with a solution of 8.5 ml (0.01 mol) of isopropylamine in 100 ml of isopropanol to 80°C for 8 hours. Thereafter the mixture is evaporated in vacuo and the resulting oil is partitioned between 100 ml of ethyl acetate and 150 ml of 0.1 N hydrochloric acid. The hydrochloric acid extract is rendered alkaline with excess sodium carbonate solution and extracted with ethyl acetate. Washing of the extract with water, drying over sodium sulphate and evaporation of the crude 1-[p-(2-methoxycarbonylaminovinyl)-phenoxy]-2-hydroxy-3-isopropylamino-propane in vacuo yields crystals of melting point 128°–129°C from acetone-ether.

Its salts can be manufactured from this compound analogously to Example 2.

1-[p-(2-Methoxycarbonylaminovinyl)phenoxy]-3-chloro-propanol-2, used as the starting material, can be manufactured as follows:

A suspension of 23.5 g (0.1 mol) of p-(2-methoxycarbonylaminovinyl)-acetoxybenzene in 300 ml of absolute methanol, which is mixed with a solution of 5.4 g of sodium methoxide in 30 ml of methanol, is warmed to 50°C for 15 minutes. Thereafter the mixture is evaporated to dryness under reduced pressure. The resulting crude sodium salt of [2-methoxy-carbonylaminovinyl]-phenol is dissolved in 100 ml of water, 50 ml of 2 N hydrochloric acid are added to the solution and the phenol which has separated out is extracted with ethyl acetate. The organic phase is washed with water, dried over sodium sulphate and evaporated in vacuo. Crude p-(2-methoxy-carbonylaminovinyl)-phenol is obtained as an oil. This can be used, as shown below, without further purification.

A sample crystallised from ether showed a melting point of 169°–170°C.

9.66 g (0.05 mol) of crude p-(2-methoxycarbonylamino-vinyl)-phenol, 0.2 ml of piperidine and 30 ml of epichlorohydrin are heated to 100°C for 12 hours. The excess epichlorohydrin is then removed under reduced pressure and the oil which remains as the residue is dissolved in chloroform and shaken with 4 N hydrochloric acid. the chloroform solution is washed with water, dried over sodium sulphate and evaporated in vacuo. The residue obtained is 1-[p-(2-methoxy-carbonylaminovinyl)-phenoxy]-3-chloro-propanol-2, in the form of an oil.

EXAMPLE 15

5.0 g of crude 1-[p-(2-methoxycarbonylaminovinyl)-phenoxy]-2-hydroxy-3-amino-propane is heated with a solution of 2.6 g (0.021 mol) of isopropyl bromide and 2.14 g (0.021 mol) of diisopropylamine in 100 ml of butanone for 24 hours under reflux, whilst stirring. The mixture is then evaporated in vacuo and the residue is partitioned between 100 ml of ethyl acetate and 20 ml of half-saturated sodium carbonate solution. The ethyl acetate extract is evaporated in vacuo. Crude 1-[p-(2-methoxycarbonylaminovinyl)-phenoxy]-2-hydroxy-3-isopropyl-amino-propane is obtained which in acetone, on addition of N-cyclohexylsulphamic acid, yields N-cyclo-hexylsulphamate of melting point 115°–116°C.

1-[p-(Methoxy-carbonylaminovinyl)-phenoxy]-2-hydroxy-3-amino-propane, used as the starting material, can be manufactured by heating a suspension of 5.0 g (0.02 mol) of 1-[p-(2-methoxycarbonylaminovinyl)-phenoxy]-2,3-epoxy-propane in 50 ml of methanol with a solution of 17 g of ammonia and 100 ml of methanol to 60°C for 2 hours in a stirred autoclave. Thereafter the mixture is evaporated in vacuo, whereupon crude 1-[4-(2-methoxycarbonylaminovinyl)-phenoxy]-2-hydroxy-3-amino-propane is obtained.

EXAMPLE 16

2.5 g (0.01 mol) of 1-[p-(2-methoxycarbonylaminovinyl)-phenoxy]-2,3-epoxy-propane and 3.6 g (0.03 mol) of β-aminobutyric acid ethyl ester in 25 ml of acetonitrile are heated to the refluxing temperature for 36 hours. After evaporation, and removal of the volatile constituents under reduced pressure, crude 1-[p-(2-methoxycarbonylaminovinyl)-phenoxy]-2-hydroxy-3-(2-ethoxycarbonyl-1-methyl-ethylamino)-propane is left From this, its N-cyclohexylsulphamate, melting point 104°–106° when recrystallised from acetone, is obtained after dissolving in isopropanol and adding the calculated amount of N-cyclohexyl-sulphamic acid.

EXAMPLE 17

4.45 g (0.0146 mol) of 1-[2-allyloxy-4-(2-methoxycarbonylaminovinyl)-phenoxy]-2,3-epoxy-propane are heated with a solution of 1.26 ml (0.0146 mol) of isopropylamine in 100 ml of isopropanol for 3 hours under reflux to 80°C. The mixture is then evaporated under reduced pressure and the resulting crude base is crystallised from acetone-ether. 1-[2-Allyloxy-4-(2-methoxycarbonylaminovinyl)-phenoxy]-2-hydroxy-3-isopropylamino-propane of melting point 91°–92° is obtained. From this, the fumarate, melting point 169°–170° (after recrystallisation from methanol-isopropanol) is obtained after dissolving in isopropanol and adding the calculated amount of fumaric acid.

1-[2-Allyloxy-4-(2-methoxycarbonylaminovinyl)-phenoxy]-2,3-epoxy-propane, used as the starting material, can be obtained as follows:

149 g (1 mol) of o-allyloxyphenol and 180 g (1.22 mols) if chloral are fused by gentle warming, 100 g of finely powdered sodium carbonate are added at 25°C and the mixture is subsequently stirred for 8 hours. The resulting viscous mass is stored for 5 days at room temperature and then introduced into 500 ml of water. The whole is thoroughly stirred, the water is decanted and washing is repeated three more times, with 250 ml of water at a time. The viscous oil which remains is crude 2-allyloxy-4-(1-hydroxy-2-trichloro-ethyl)-phenol. This is introduced into a solution of 250 g of potassium hydroxide in 500 ml of methanol at 30°C over the course of 2–3 hours and the reaction mixture is left to stand for 3 hours. The alkali metal salts which have precipitated are filtered off and the filtrate is evaporated under reduced pressure. The oily residue is converted into a slurry with ice water, acidified with hydrochloric acid and extracted with chloroform. The chloroform extract is washed with water, dried over sodium sulphate and then filtered through a 3 cm thick layer of Merck silica gel (0.063–0.20). After washing with chloroform, evaporation of the filtrate under reduced pressure and crystallisation of the residue from hexane yields 3-allyloxy-4-hydroxy-benzaldehyde of melting point 66°–67°C.

48.5 g (0.27 mol) of 3-allyloxy-4-hydroxy-benzaldehyde, 104 g (1 mol) of malonic acid, 140 ml of pyridine and 4 ml of piperidine are heated to 100°C for 2 hours, whilst stirring. The volatile constituents are distilled off under reduced pressure at 80°C and the residue is stirred with 800 ml of water. The crystals obtained are filtered off and recrystallised from methylene chloride. 3-Allyl-4-hydroxy-cinnamic acid of melting point 132°–133°C is obtained.

115.5 g (0.525 mol) of 3-allyloxy-4-hydroxy-cinnamic acid are dissolved in 530 ml of 2 N sodium hydroxide solution, 800 g of ice are added and 107 g (1.05 mols) of acetic anhydride are introduced dropwise over the course of quarter of an hour at 0°–5°C, whilst stirring. The crystals which have precipitated are then filtered off, suction-dried and recrystallised from chloroform. 3-Allyloxy-4-acetoxy-cinnamic acid of melting point 154°–155°C is obtained.

26.2 g (0.1 mol) of 3-allyloxy-4-acetoxy-cinnamic acid are suspended in 90 ml of benzene and 14.6 ml (0.2 mol) of thionyl chloride are added. The reaction mixture is heated to the boil under reflux for 30 minutes. Thereafter the solvent and the excess thionyl chloride are removed by distillation under reduced pressure. The crude 3-allyloxy-4-acetoxy-cinnamic acid chloride which is left is dissolved in 100 ml of absolute dimethoxyethane, 19.5 g (0.3 mol) of sodium azide are added and the reaction mixture is subsequently stirred for 48 hours at room temperature. The inorganic salts are then filtered off and the filtrate is concentrated under reduced pressure at 30°C. Hereupon, colourless crystals separate out. The crystallisation is completed by addition of ether. 3-Allyloxy-4-acetoxy-cinnamic acid azide of melting point 83°–84°C is obtained.

7.2 g (0.025 mol) of 3-allyloxy-4-acetoxy-cinnamic acid azide are suspended in 100 ml of absolute toluene and the suspension is slowly brought to the boil, whilst stirring. The evolution of nitrogen starts at approx. 80°C; it has ended after boiling for half an hour. After cooling to room temperature, 2.05 ml (0.05 mol) of absolute methanol and a few drops of triethylamine are added. Thereafter the mixture is heated to the refluxing temperature for 18 hours, the solvent is distilled off under reduced pressure and the residue is crystallised from ether. 2-allyloxy-4-(2-methoxycarbonylaminovinyl)-acetoxy-benzene of melting point 117°–118° is obtained.

5.77 g (0.021 mol) of 2-allyloxy-4-(2-methoxycarbonyl-aminovinyl)-acetoxy-benzene are suspended in 75 ml of absolute methanol, a solution of 1.14 g (0.021 mol) of sodium methoxide in 15 ml of absolute methanol is added and the mixture is subsequently warmed to 50°C for 15 minutes. Thereafter it is evaporated to dryness under reduced pressure. The resulting crude sodium salt of 2-allyloxy-4-(2-methoxycarbonylaminovinyl)-phenol is heated to the boil with 20 ml of epichlorohydrin for 24 hours under a reflux condenser and whilst stirring. Thereafter the excess epichlorohydrin is removed by distillation under reduced pressure and the residue is partitioned between water and methylene chloride. The organic phase is separated off, dried over sodium sulphate and evaporated. After crystallisation of the crude product, thus obtained, from ether, 1-[2-allyloxy-4-(2-methoxycarbonylaminovinyl)-phenoxy]-2,3-epoxy-propane of melting point 135°–136° is obtained.

EXAMPLE 18

Tablets containing 60 mg of active substance are manufactured, in the usual manner, to have the following composition:

| Composition | |
|---|---|
| 1-[p-(2-Methoxycarbonylaminovinyl)-phenoxy 2-hydroxy-3-isopropylamino-propane fumarate | 60 mg |
| Wheat starch | 59 mg |
| Lactose | 60 mg |
| Colloidal silica | 10 mg |
| Talc | 10 mg |
| Magnesium stearate | 1 mg |
| | 200 mg |

Manufacture

1-[p-(2-Methoxycarbonylaminovinyl)-phenoxy]-2-hydroxy-3-isopropylamino-propane fumarate is mixed with a part of the wheat starch, with lactose and with colloidal silica and the mixture is forced through a sieve. A further part of the wheat starch is worked into a paste with a 5-fold amount of water on a water bath, and the powder mixture is kneaded with this paste until a slightly plastic mass has been produced.

The plastic mass is forced through a sieve of approx. 3 mm mesh width and dried, and the resulting dry granules are again forced through a sieve. Thereafter the remaining wheat starch, talc and magnesium stearate are mixed in and the mixture is pressed to give tablets weighing 200 mg and having a breaking groove.

The daily dose is about ½ to 4 tablets in the case of a warm-blooded animal of approx. 75 kg body weight, and it is also possible to administer the corresponding dose of active substance in a single tablet of appropriate composition.

Tablets containing 60 mg of 1-[2-allyl-(4-methoxycarbonylaminovinyl)-phenoxy]-2-hydroxy-3-isopropylamino-propane fumarate or containing 1-[2-allyl-4-(2-acetylamino-vinyl)-phenoxy]-2-hydroxy-3-isopropylamino-propane-N-cyclohexyl-sulphamate as the active substance can be manufactured analogously.

We claim:

1. Amines of the formula I

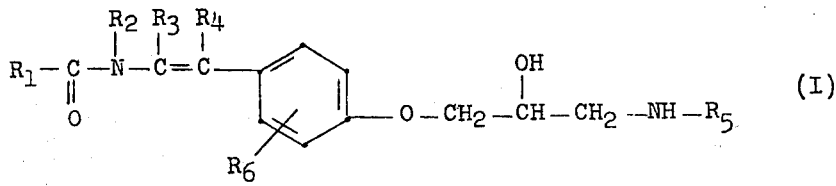

wherein $R_1$ is lower alkoxy, $R_2$ is hydrogen or lower alkyl, $R_3$ is hydrogen, lower alkyl, carboxyl or lower alkoxycarbonyl, $R_4$ is hydrogen or lower alkyl, $R_5$ is lower alkyl, phenyl optionally substituted by lower alkyl, lower alkoxy, halo or trifluoromethyl, carboxy-lower alkyl esterified with an aliphatic alcohol, carbamoyl-lower alkyl, N-mono-lower alkyl carbamoyl-lower alkyl, or N,N-di-lower alkyl carbamoyl-lower alkyl, and $R_6$ denotes halogen, trifluoromethyl, lower alkyl, lower alkenyl, lower alkoxy, lower alkenyloxy, nitro, lower alkoxymethyl, carbamoyl, N-lower alkylcarbamoyl, lower alkinyloxy or hydrogen, and therapeutically acceptable acid addition salts thereof.

2. Amines as claimed in claim 1, of the formula I, wherein $R_1$ is lower alkoxy, $R_2$ is hydrogen or lower alkyl, $R_3$ is hydrogen, lower alkoxycarbonyl or carboxyl, $R_4$ is hydrogen or lower alkyl with up to 4 carbon atoms, $R_5$ is α-branched lower alkyl or a group of the formula

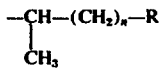

wherein $n$ is 0, 1 or 2 and R is phenyl which is optionally substituted by $R_6$, or is carboxyl, lower alkoxycarbonyl, carbamoyl, N-lower alkylcarbamoyl, N,N-di-lower alkylcarbamoyl, or N,N-di-lower alkylcarbamoyl-lower alkyl, and $R_6$ is hydrogen, halogen, lower alkoxy, lower alkenyl or lower alkenyloxy, and therapeutically acceptable acid addition salts thereof.

3. Amines as claimed in claim 1, of the formula I, wherein $R_1$ is lower alkoxy with up to 4 carbon atoms, $R_2$ is hydrogen, $R_3$ is hydrogen, $R_4$ is hydrogen, $R_5$ is α-branched lower alkyl with 3 to 6 carbon atoms or a group of the formula

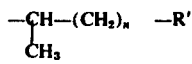

wherein $n'$ is 0 or 1 and $R'$ is benzyl which is optionally substituted by $R_6$, or is carboxyl, methoxycarbonyl, ethoxycarbonyl, carbamoyl, N-methylcarbamoyl, or N,N-dimethylcarbamoyl, and $R_6$ is hydrogen, chlorine, bromine, lower alkoxy with up to 4 carbon atoms, lower alkenyl with 2 to 5 carbon atoms or lower alkenyloxy with 3 to 5 carbon atoms, and therapeutically acceptable acid addition salts thereof.

4. Amines as claimed in claim 1, of the formula I, wherein $R_1$ denotes lower alkoxy with up to 4 carbon atoms, $R_2$ is hydrogen or methyl, $R_3$ is hydrogen, carboxyl or carbomethoxy, $R_4$ is hydrogen, $R_5$ is α-branched lower alkyl with 3 or 4 carbon atoms or a group of the formula

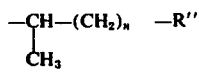

wherein $n'$ is 0 to 1 and $R''$ is benzyl which is optionally substituted by $R_6$, or is methoxycarbonyl or carbamoyl, and $R_6$ denotes hydrogen, methoxy or ethoxy, chlorine, allyl, methallyl or propenyl-1, allyloxy or methallyloxy, and therapeutically acceptable acid addition salts thereof.

5. Amines as claimed in claim 1, of the formula I, wherein $R_1$ is methoxy, ethoxy or n-butoxy, $R_2$ is hydrogen, $R_3$ is hydrogen, $R_4$ is hydrogen, $R_5$ is isopropyl, tert.-butyl, 2-(3-phenyl)butyl, 2-(1-carbamoyl)-propyl, and $R_6$ is hydrogen, methoxy, chlorine, allyloxy or allyl, and therapeutically acceptable acid addition salts thereof.

6. 1-[p-(2-Methoxycarbonylaminovinyl)-phenoxy]-2-hydroxy-3-isopropylamino-propane as claimed in claim 1, or a therapeutically acceptable acid addition salts thereof.

7. 1-[p-(2-n-Butoxycarbonylaminovinyl)-phenoxy]-2-hydroxy-3-isopropylamino-propane as claimed in claim 1, or a therapeutically acceptable acid addition salts thereof.

8. 1-[2-Allyl-4-(2-methoxycarbonylaminovinyl)-phenoxy]-2-hydroxy-3-isopropylamino-propane as claimed in claim 1, or a therapeutically acceptable acid addition salts thereof.

9. 1-[2-Allyloxy-4-(2-methoxycarbonylaminovinyl)-phenoxy]-2-hydroxy-3-isopropylamino-propane as claimed in claim 1, or a therapeutically acceptable acid addition salts thereof.

10. 1-[2-Chloro-4-(2-methoxycarbonylaminovinyl)-phenoxy]-2-hydroxy-3-isopropylamino-propane as claimed in claim 1, or a therapeutically acceptable acid addition salts thereof.

11. 1-[p-(2-Methoxycarbonylaminovinyl)-phenoxy]-2-hydroxy-3-(1-methyl-3-phenyl-propylamino)-propane as claimed in claim 1, or a therapeutically acceptable acid addition salts thereof.

12. 1-[p-(2-Methoxycarbonylaminovinyl)-2-hydroxy-3-(2-carbamoyl-1-methyl-aethylamino)-propane as claimed in claim 1, or a therapeutically acceptable acid addition salts thereof.

13. A compound as claimed in claim 1, being 1-[p-(ethoxycarbonylaminovinyl)-phenoxy]-2-hydroxy-3-tertiary-butylamino propane.

* * * * *